United States Patent [19]

Bermingham

[11] 4,116,197

[45] Sep. 26, 1978

[54] DISPOSABLE FEMALE-BODY-WORN URINAL

[76] Inventor: Winifred Bermingham, 171 E. 77th St., New York, N.Y. 10021

[21] Appl. No.: 828,986

[22] Filed: Aug. 30, 1977

[51] Int. Cl.² ............................................. A61F 5/44
[52] U.S. Cl. .................................... 128/286; 128/289; 128/295
[58] Field of Search ............... 128/283, 284, 286, 289, 128/288, 294, 295

[56] References Cited

U.S. PATENT DOCUMENTS

| 660,388 | 10/1900 | Moberg et al. | 128/286 |
|---|---|---|---|
| 913,983 | 3/1909 | Scheller et al. | 128/286 |
| 3,890,973 | 6/1975 | Davis et al. | 128/286 |

Primary Examiner—Robert W. Michell
Assistant Examiner—Henry S. Layton
Attorney, Agent, or Firm—Burgess, Dinklage & Sprung

[57] ABSTRACT

This invention provides a disposable urinal to be worn by female incontinent patients. It consists of an adjustable belt having a flexible sheet attached thereto. A urine collecting pouch depends from the sheet, with a disposable vaginal pad provided between the wearer's body and the sheet.

10 Claims, 2 Drawing Figures

DISPOSABLE FEMALE-BODY-WORN URINAL

BACKGROUND OF THE INVENTION

This invention relates to disposable urinals. More particularly, it relates to disposable urinals to be worn by female incontinent patients.

It is not uncommon for female patients with bladder disorders to be incontinent and require the use of a disposable urinal. Such a urinal should provide the patient with relative freedom of movement, long periods between emptying the device, comfort and a certain amount of deodorant protection when in use. In these respects, prior art devices have been deficient.

SUMMARY OF THE INVENTION

Figures 1, 2:
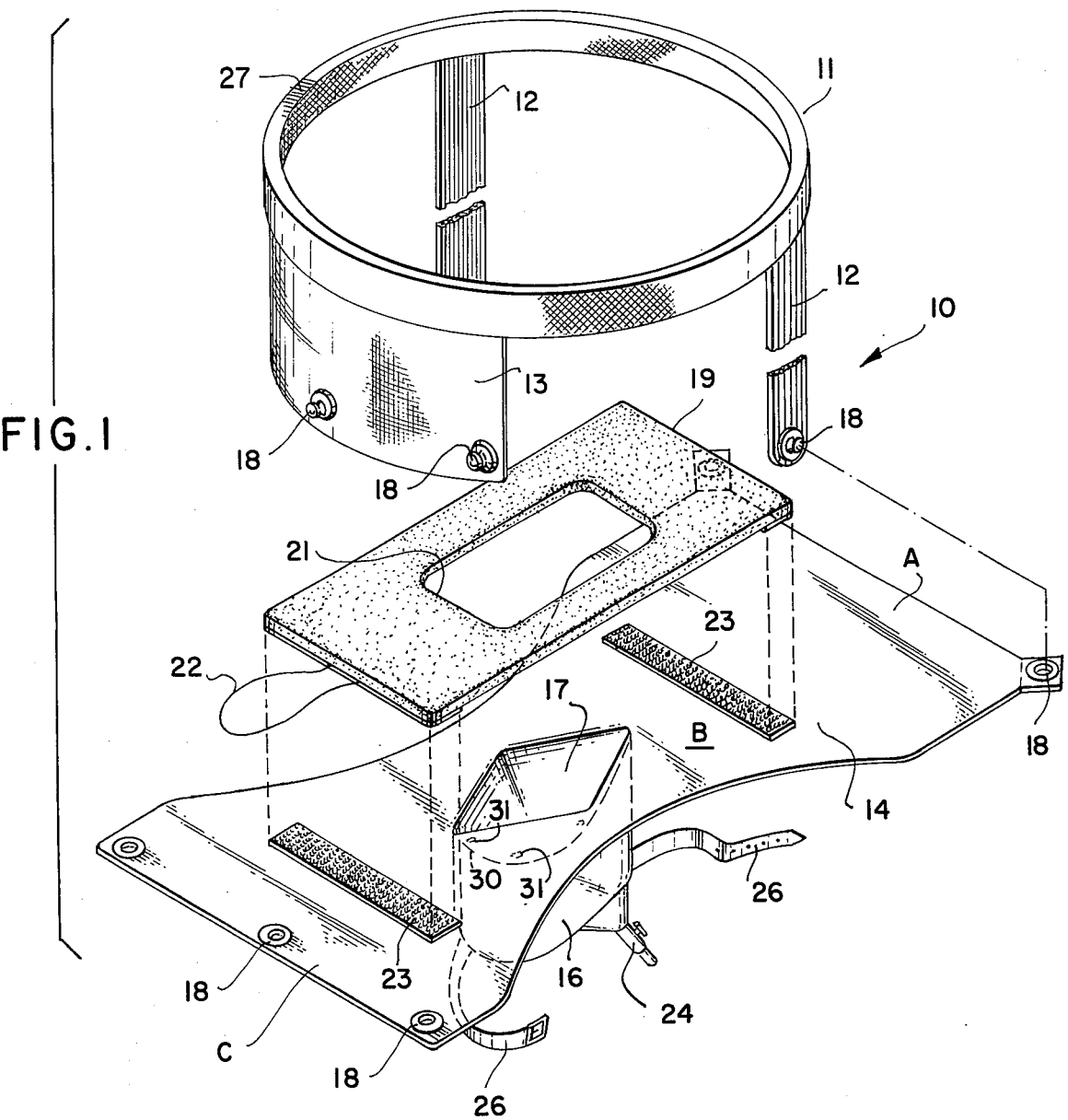
FIG. 1 is an isometric view of a urinal device of this invention shown in exploded view.
FIG. 2 is a side elevation view of the device of FIG. 1 assembled.

Broadly, the invention provides a female urinary collection device comprising a waist belt having a plurality of depending support elements with upper portions integral with the waist belt. There is also provided an elongated flexible sheet of waterproof material having front, center and rear sections. The front and rear sections are in detachable engagement with a lower portion of the support elements. The center section of the sheet having a width substantially less than that of the front or rear sections. The center section of the sheet further has a depending substantially elongated pouch integral therewith, and an opening in the center section in fluid communication with the interior of the pouch. A liquid absorbing pad is also provided which is associated with the flexible sheet and has an opening in the center thereof maintained in positional relationship with the opening in the flexible sheet. A valve is also provided at the base of the pouch in fluid communication with the interior of the pouch.

The waist belt of the urinary device has adjusting means for conforming the belt to the waist of the wearer.

The front section of the flexible sheet of the device is in detachable engagement with a pair of strap-like support elements with each of the straps engaging a corner of the sheet, and the length of the back edge of the rear section of the sheet is in detachable engagement with an apron like supporting element. The straps and the apron of the device are detachably mounted on the flexible sheet with a plurality of snap fasteners.

The absorbing pad and the flexible sheet have mutual engaging means for maintaining the pad in association with the sheet.

The absorbing pad also has an extending loop of flexible material at its rearward edge corresponding to the rear section of the flexible sheet, with the loop encircling at least one of the rear snap fasteners.

The urinary device also provides a strap afixed on the pouch for straping the pouch to one of the legs of the user of the device.

The opening in the absorbant pad is also in substantial conformity with the opening in the flexible sheet.

The opening in flexible sheet may comprise a diaphragm having a plurality of apertures therethrough.

The absorbant pad may also have a deodorant material incorporated in it.

DESCRIPTION OF THE PREFERRED EMBODIMENT

Referring to FIG. 1 there is shown generally at 10 the female urinary device of this invention. It comprises a waist belt 11, having at the front a pair of depending support elements e.g. straps 12 and an apron-like support element 13 at the rear of the belt 11.

A flexible sheet of waterproof material 14 e.g. flexible plastic such as polyethylene or polyvinylchloride is positioned under the belt 11 and between the legs of the wearer. The sheet 14 has these sections, front A, center B, and rear C. The center section B has a width which is substantially less than that of either the front section A or the rear section C. This is to provide a better fit for the wearer. Located approximately at the center of section B is a depending pouch 16. The sheet 14 has an opening 17 which is in fluid communication with the pouch 16.

The sheet 14 is detachably received to the straps 12 and apron 13 by a series of snap fasteners 18 (shown in detached position in FIG. 1).

The device 10 is also provided with a disposable absorbant pad 19 which has an opening 21 corresponding with the sheet opening 17. The pad 19 is held in position on the sheet 14 by means of a loop 22 which goes around a fastener 18 and by other conventional fasteners such as a velcro fastener 23.

The pouch 16 is also provided with a valve 24 for emptying the pouch 16 of collected urine. The valve may be of conventional design. A strap 26 is provided on the pouch 16 for fastening the pouch to one leg of a wearer.

The waist belt 11 is also provided with an adjustment means 27, such as a flexible plastic insert or a buckle.

It is also within the scope of this invention to provide for a deodorant material to be incorporated in the disposable pad 19. Conventional deodorants may be used, and they can be sprayed on, impregnated in the pad 19 or be in microcapsule form which releases the deodorant under body heat or pressure.

In use, the device 10 is strapped about the waist of the wearer by using the belt 11 the pad 19, sheet 14 and pouch 16 are positioned between the wearer's legs and about her genitals. The pouch 16 is designed to accommodate a volume of urine that may be emptied at intervals while being worn. It may be conveniently emptied by means of valve 24 into any suitable receptacle.

The device 10 is suitable for both ambulatory and bedbound patients. May require changing only every 24 hours. It is non-spilling and the pouch 16 may be transparent for easy noting of urine volume and additionally the pouch 16 may be marked in volume gradations to indicate the amount of urine voided.

The sheet 14 and the pouch 16 may be conveniently heat sealed together.

It is also an aspect of this invention that the opening 17 in the pouch 16 may be a diaphragm 30 having a plurality of apertures 31 therethrough. This would constitute a sieve-like arrangment and be an aid in preventing spillage of the urine in the pouch 16.

What is claimed is:

1. A female urinary collection device comprising, a waist belt having a plurality of depending support elements with upper portions integral with the waist belt, an elongated flexible sheet of waterproof material having front, rear and center sections, the front and rear sections in detachable engagement with a lower portion of the support elements, the center section of the sheet having a width substantially less than that of the front section and the rear section, the center section of the sheet further having a depending substantially elongated pouch integral therewith, an opening in the center section in fluid communication with the interior of the pouch, a liquid absorbing pad associated with the flexible sheet and having an opening in the center thereof maintained in positional relationship with the opening in the flexible sheet, mutual engaging means on the absorbing pad and the flexible sheet for releasably maintaining the pad in association with the sheet, and a valve at the base of the pouch, in fluid communication with the interior of the pouch.

2. The urinary collection device according to claim 1 wherein the waist belt has adjusting means for conforming the belt to the waist of a wearer.

3. The urinary collection device according to claim 2 wherein the front section of the flexible sheet is in detachable engagement with a pair of strap-like support elements with each of the straps engaging a corner of the sheet and the length of the back edge of the rear section of the flexible sheet in detachable engagement with an apron-like supporting element.

4. The urinary collection device according to claim 3 wherein the straps and the apron are detachably mounted on the flexible sheet with a plurality of snap fasteners.

5. The urinary collection device according to claim 4 wherein the absorbing pad has an extending loop of flexible material at its rearward edge corresponding to the rear section of the flexible sheet, the loop encircling at least one of the rear snap fasteners.

6. The urinary collection device according to claim 5 wherein a strap is affixed on the pouch for straping the pouch to one of the legs of the user of the collective device.

7. The urinary collection device according to claim 6 wherein the opening in the absorbant pad is in substantial conformity with the opening in the flexible sheet.

8. The urinary collection device according to claim 7 wherein the opening in the flexible sheet comprises a diaphragm having a plurality of apertures therethrough.

9. The urinary collection device according to claim 8 wherein a deodorant material is incorporated in the absorbant pad.

10. A female urinary collection device comprising, a waist belt having a plurality of depending support elements with upper portions integral with the waist belt, an elongated flexible sheet of waterproof material having front, rear and center sections, the front and rear sections in detachable engagement with a lower portion of the support elements, the center section of the sheet having a depending pouch integral therewith, an opening in the center section in fluid communication with the interior of the pouch, a diaphragm disposed in the opening and having a plurality of apertures therethrough, a liquid absorbing pad having an opening in the center thereof and removably mountable on the flexible sheet to maintain the opening in the pad in alignment with the opening in the flexible sheet, and a valve at the base of the pouch in fluid communication with the interior of the pouch.

* * * * *